(12) United States Patent
Crudden et al.

(10) Patent No.: US 8,083,851 B2
(45) Date of Patent: Dec. 27, 2011

(54) ANTIMICROBIAL CEMENTS AND CEMENTITIOUS COMPOSITIONS

(75) Inventors: Joseph J. Crudden, Hudson, NH (US); Joseph V. Lazzaro, Hampstead, NH (US); Edward K. Welch, II, Naples, FL (US)

(73) Assignee: Sciessent LLC, Wakefield, MA (US)

( * ) Notice: Subject to any disclaimer, the term of this patent is extended or adjusted under 35 U.S.C. 154(b) by 897 days.

(21) Appl. No.: 11/648,388

(22) Filed: Dec. 29, 2006

(65) Prior Publication Data
US 2008/0156232 A1 Jul. 3, 2008

(51) Int. Cl.
*C04B 14/34* (2006.01)
*C04B 16/00* (2006.01)

(52) U.S. Cl. ........ 106/724; 106/733; 106/738; 106/772; 106/778; 501/141

(58) Field of Classification Search .......... 106/772, 106/724, 733, 738, 778; 501/141
See application file for complete search history.

(56) References Cited

U.S. PATENT DOCUMENTS

| | | | |
|---|---|---|---|
| 4,211,680 A | 7/1980 | Shearing | |
| 5,089,275 A * | 2/1992 | Antelman | 424/602 |
| 5,421,867 A * | 6/1995 | Yeager et al. | 106/18.32 |
| 5,698,229 A * | 12/1997 | Ohsumi et al. | 424/604 |
| 6,752,857 B1 | 6/2004 | Birdwell | |
| 6,767,647 B2 * | 7/2004 | Swofford et al. | 428/537.7 |
| 6,773,822 B2 * | 8/2004 | Capps | 428/537.7 |
| 6,777,103 B2 * | 8/2004 | Merkley et al. | 428/532 |
| 6,884,741 B2 * | 4/2005 | Batdorf | 442/123 |
| 6,893,752 B2 * | 5/2005 | Veeramasuneni et al. | 428/703 |
| 7,056,582 B2 * | 6/2006 | Carbo et al. | 428/402 |
| 7,294,189 B2 * | 11/2007 | Wantling | 106/164.3 |
| 7,488,383 B2 * | 2/2009 | Donlon et al. | 106/772 |
| 7,632,348 B2 * | 12/2009 | Cowan et al. | 106/724 |
| 2004/0121140 A1 | 6/2004 | Ramirez Tobias et al. | |
| 2005/0106336 A1 | 5/2005 | Ong et al. | |
| 2006/0171976 A1 * | 8/2006 | Weir et al. | 424/405 |
| 2006/0267234 A1 | 11/2006 | Ong et al. | |
| 2006/0272542 A1 * | 12/2006 | Horner et al. | 106/15.05 |

FOREIGN PATENT DOCUMENTS

| | | |
|---|---|---|
| GB | 1192864 | 5/1970 |
| GB | 1342063 | 12/1973 |
| JP | 04-154651 | 5/1992 |
| JP | 06-041516 | 2/1994 |
| JP | 06-247820 | 9/1994 |
| JP | 06-256052 | 9/1994 |
| JP | 09-002849 | 1/1997 |
| JP | 09-060768 | 3/1997 |
| JP | 11-029375 | 2/1999 |
| JP | 11-079920 | 3/1999 |
| JP | 11-157907 | 6/1999 |
| JP | 11-171629 | 6/1999 |

OTHER PUBLICATIONS

JP 2002103510 (Sakagami) Apr. 9, 2002 abstract only.*

(Continued)

*Primary Examiner* — Paul Marcantoni
(74) *Attorney, Agent, or Firm* — Edward K. Welch, II; IP&L Solutions

(57) ABSTRACT

Efficient antimicrobial additives are provided comprising a wettable, cake-forming inorganic material having dispersed therein an inorganic or organometallic antimicrobial agent capable of releasing antimicrobial metal ions. These antimicrobial additives are especially effective for use in cements, mortars and cementitious compositions.

36 Claims, 1 Drawing Sheet

OTHER PUBLICATIONS

KR 2006056560 (Choi et al.) May 25, 2006) abstract only.*
JP 62267212 (Yoshida) Nov. 19, 1987 abstract only.*
WO 2006089654 Wachtler et al. (Aug. 31, 2006) abstract only.*
KR 2006109006 (Yang) Oct. 19, 2006 abstract only.*
JP 08225415 (Iwasaki et al.) Sep. 3, 1996 abstract only.*
KR 2003025719 (Kim et al.) Mar. 29, 2003) abstract only.*

* cited by examiner

US 8,083,851 B2

ANTIMICROBIAL CEMENTS AND CEMENTITIOUS COMPOSITIONS

FIELD OF THE INVENTION

The present invention relates to inorganic antimicrobial additives and mortars, cements and cementitious compositions having excellent antimicrobial and/or antifungal properties comprising said additives. In particular there are provided improved antimicrobial mortar, cement and cementitious products wherein the improvement comprises an antimicrobial agent in the form of discrete particles of a wettable, caked inorganic material having dispersed therein an inorganic antimicrobial agent.

BACKGROUND OF THE INVENTION

Cements, mortars, and cementitious compositions are well known and widely available. Their make-up and properties vary widely enabling many and varied end-use applications. For example, many cements, mortars and cementitious compositions are employed in structural applications for buildings, roadways, bridges, wall construction, boat hulls, walkways, and the like. Additionally, they have many applications in non-structural applications, some of which are functional, for example, floor coatings, roofing tiles, furniture, urns, ornaments, and the like, and others non-functional, such as stucco, skim-coat, and other wall coatings, the latter being mostly decorative in nature.

Cements, mortars and cementitious compositions have and continue to evolve as the applications and demands of those applications expand. Oftentimes the evolution takes the form of a variation in the formulation, i.e., using the same constituents in different amounts. Other times the evolution takes the form of new formulations altogether, especially those employing newly identified ingredients that provide new and/or enhanced properties not otherwise attainable. Perhaps one of the most significant advancements in cements and mortars has been the addition of curable/polymerizable organic materials, especially urethane-based and/or epoxy-based materials to the traditionally inorganic mix of the cement, mortar or cementitious composition. Such compositions are described in, for example, Shearing et. al.—U.S. Pat. No. 3,763,070 and U.S. Pat. No. 4,211,680 and Alexander et. al.—U.S. Pat. No. 4,127,548, and provide fast setting, highly durable surfaces, especially for floorings.

Despite the strength and durability of these materials, a number of environmental factors greatly affect their longevity. For example, for those end-use applications exposed to the outdoors environment, acid rain and deicing salts and like compositions degrade and breakdown the hardened cements, mortars and cementitious compositions. However, perhaps the most insidious bad actor on hardened cements, mortars and cementitious compositions are microbes, namely bacteria, molds, mildew, algae and the like. These microbes, particularly certain bacteria, readily degrade the hardened cements, mortars and cementitious compositions. Others, especially, the molds, mildew and algae, render them unsightly and may introduce health concerns as well.

An area of particular concern is in cement, mortar and cementitious flooring systems. Such flooring systems find wide use in food and food processing facilities, pharmaceutical and biopharmaceutical facilities, and research, especially biotechnology, facilities due to their high durability. This is because such flooring must be washed repeatedly with highly caustic solutions to ensure the removal of all bacteria and the like to avoid contamination of food stocks and pharmaceuticals and related processing equipment and the like as well as to maintain containment of micro-organisms employed in bio-pharmaceutical and biotechnology applications.

Over the years, many different attempts have been made to provide antimicrobial performance and characteristics to cements, mortars and cementitious compositions. Maeda et. al.—JP 04-149053 and Hori et. al. JP 11-079920 describe the addition of difficult to dissolve metals and metallic oxides and water soluble metal compounds, respectively, into concretes, mortars and the like used in sewer systems to attack sulfur oxidative bacteria. Atsumi et. al., JP 04-154651 describe the addition of silver, copper or zinc containing calcium phosphate-based compounds, especially tricalcium phosphate and hydroxyapatite, to traditional mortars for producing mildew-proofing joint filling materials. Similarly, Yamazaki et. al.—JP 11-171629 describes the addition of an antimicrobial metal containing hydroxyapatite to mortar and concrete slurries for instilling antimicrobial properties to the hardened materials. Haraguchi—JP 11-157907 describes a mortar composition containing, among the traditional components, an aqueous resin emulsion and an antimicrobial agent. Morioka—JP 09-002849 describes forming calcium aluminate-based glass powders containing antimicrobial metal salts as antimicrobial/antimildew additives for hydraulic cements. Shigeru et. al.—JP 06-256052 and JP 06-247820 describe various cements and gypsum having incorporated therein cuprous oxide alone or in combination with a silver-containing powder for alga-proofing, antifungal and antimicrobial effects. Ong et. al.—US 2005/0106336 A1 describe cementitious slab products formed from a composite material of a natural aggregate, a cementitious matrix and an antimicrobial agent. Haraguchi JP 11-029375 describes a surface finishing material for mortars and cements comprising an antimicrobial agent compounded into a cement mortar. Additionally, Ramirez Tobias et. al. describe concrete-based floor and wall coverings having an organic antimicrobial agent incorporated therein.

While such efforts have helped control bacterial, mildew and algal growth, the use of such antimicrobial additives is at a cost, not just financially, but also with respect to the properties of the cement, mortar and cementitious materials themselves. In order to achieve reasonable, commercial performance, considerably high loadings of the antimicrobial additives is necessary. This adds significant costs to an otherwise low cost product. Additionally, as one adds more and more antimicrobial agents to enhance their intended performance, there is an effect on the properties of the modified materials, especially on their color and appearance. Thus, there is still a need for an antimicrobial additive and antimicrobial cements, mortars and cementitious compositions that have high antimicrobial performance relative to their level of incorporation. Additionally, there is a need for such compositions that have enhanced antimicrobial performance with the same or less antimicrobial additive than found with the mere addition of such additives as described in the art.

SUMMARY OF THE INVENTION

The present invention relates to novel antimicrobial additives for cements, mortars, cementitious compositions and hybrid cementitious compositions as well as to the modified cements, mortars, cementitious compositions and hybrid cementitious compositions containing the novel antimicrobial additives. Specifically, the present invention relates to discrete particles of a wettable, caked inorganic material having dispersed therein an inorganic antimicrobial agent capable of releasing antimicrobial metal ions in the presence of water. Preferred antimicrobial agents are either water soluble or of the ion-exchange type. The wettable, caked inorganic material is preferably a gypsum or gypsum-like material or a clay or clay-like material that is readily wetted and absorbs sufficient water to allow the antimicrobial agent to release its antimicrobial metal ions.

The present invention also pertains a method of forming the novel antimicrobial additives of the present invention, said method comprising the steps of adding the antimicrobial agent to an inorganic wettable cake forming composition; allowing the composition to cure or harden to form the cake; and breaking, crushing and/or grinding the cake to form discrete particles thereof. Preferably, the crushed and ground cake composition is screened to remove undesirably large particles and/or isolate the desired particle sized materials for use.

The present invention also pertains to antimicrobial cements, mortars cementitious compositions and hybrid cementitious compositions having incorporated therein or, in the case of multi-part or component systems, in a component thereof the aforementioned novel antimicrobial additive particles. Especially preferred and applicable cements, mortars and cementitious compositions are those hybrid systems comprising a conventional cement, mortar or cementitious composition and a curable or polymerizable organic component(s), such as epoxies, polyurethanes, polyesters, methacrylates, vinyl esters and the like, especially curable epoxy or polyurethane component(s): these compositions altogether referred to as "hybrid cementitious compositions" herein and in the appended claims.

Finally, the present invention also pertains to structures, products, articles of manufacture, finished goods and surface finishes, and the like comprising the aforementioned cured antimicrobial cements, mortars, cementitious compositions and hybrid cementitious compositions.

DETAILED DESCRIPTION

Figure 1:
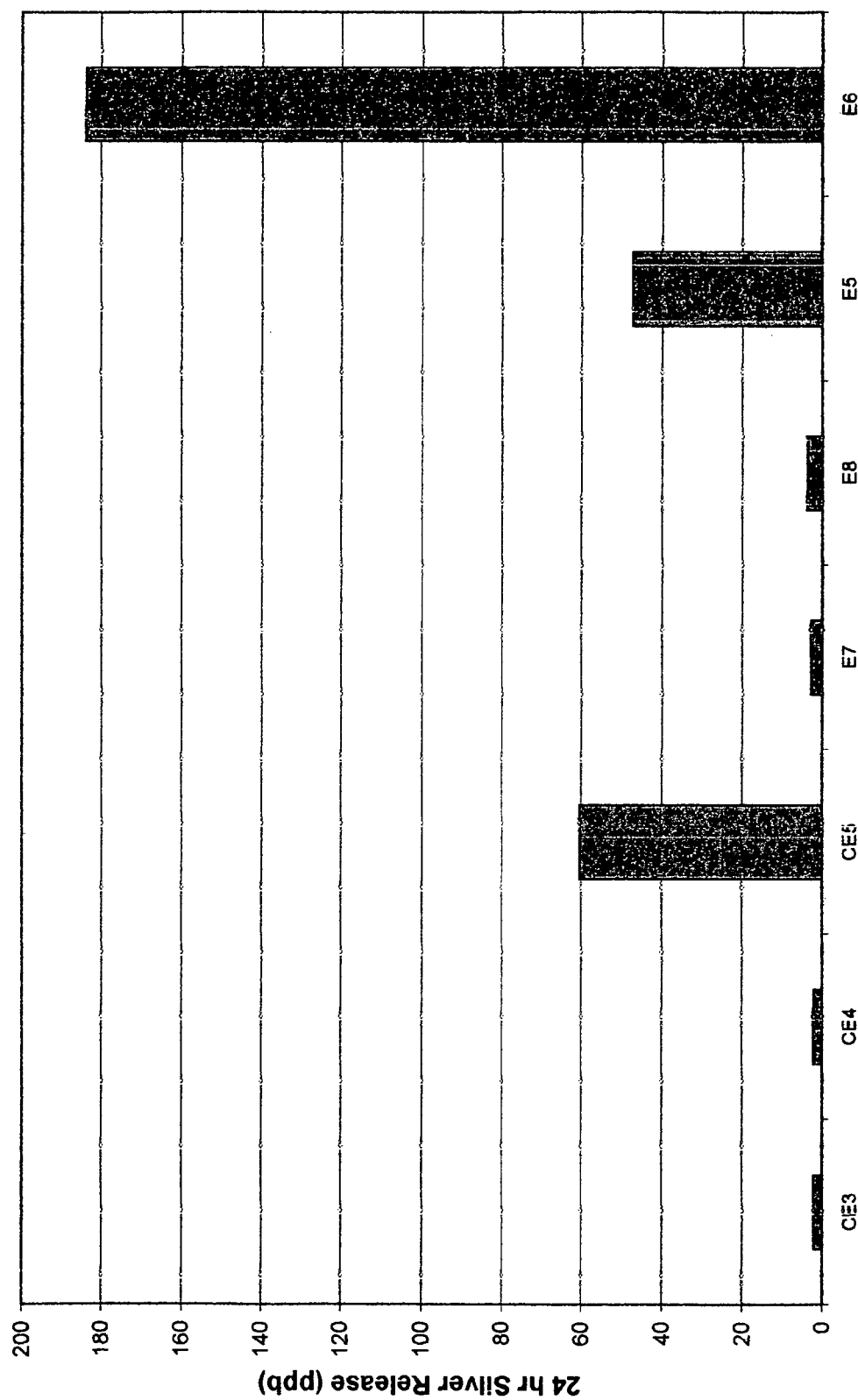
FIG. 1 shows a bar chart of ion release of various compositions within and outside the scope of the present invention.

As used herein and in the appended claims, the term "wettable" when used in relation to the novel antimicrobial additive particles of the present invention refers not only to the ability of the particles to be surface wetted but also to their ability to absorb water into the particles themselves. The extent of water absorption depends upon the porosity within and at the surface of the particles and the extent to which such pores are interconnected. Similarly, as used herein and in the appended claims, the terms "cake", "caked" or "cake mass" refers to the conventionally powdered inorganic material in a solid mass, the solid mass resulting from treatment of the powdered mass with heat, pressure, water and/or carbon dioxide, which solid mass is able to maintain its structure under moderate to low pressure or when placed in water for up to one-half hour, or both, i.e., is able to maintain, for the most part, the cake structure when subjected to the mixing step associated with their use upon incorporation into a matrix material such as cements and the like. For example, it is preferred that the cake not readily crumble and return to a powdered or granular state when subjected to compression in one's hand or when placed in water (like cubed sugar). Most preferably, the cake will withstand such pressure but may loose its cake structure when pressed under foot of a typical person, e.g., under pressures as low as 25 ft.lbs/in$^2$. Other cakes may withstand even higher pressures, especially in those cakes that are formed by high temperature firing, such as the clays and like ceramic materials. Conversely, suitable fired materials also include those that may crumble under hand pressure so long as the mixing forces to which they are subjected to during the incorporation step are insufficient to substantially break down the wettable, caked antimicrobial particles.

Suitable inorganic materials are those that are capable of forming a wettable cake and which do not contain species, reactive groups and the like which are reactive with the antimicrobial metal ions or, if so, that are not present to an extent that they will markedly deplete the available antimicrobial metal ions needed for providing antimicrobial properties. Exemplary inorganic materials include gypsum (calcium sulfate), gypsum cements (cements consisting essentially of calcium sulfate), calcium hydroxide, calcium carbonate, clay, kaolin clay, china clay, calcite, chalk, kalsomine (whitewash), porous Portland cement, and the like. These inorganic materials may be used in their hydrated form, hemi-hydrated form or following drying (anhydrous form). Especially preferred are the gypsum and gypsum cements.

Suitable antimicrobial agents are essentially any of those antimicrobial metals or metal ion sources that are capable of releasing the antimicrobial metal ion in the presence of water. Antimicrobial metals and metal ions include silver, copper, zinc, tin, gold, mercury, lead, iron, cobalt, nickel, manganese, arsenic, antimony, bismuth, barium, cadmium, chromium and thallium. Metals and metal ions of silver, copper, zinc, and gold are preferred because they are considered safe for in vivo use. Silver ions are more preferred due to the fact that they have the highest ratio of efficacy to toxicity, i.e., high efficacy to low toxicity; though combinations of silver with zinc or copper or both have recently been shown to have improved efficacy and/or color stability as compared to silver alone.

Although the antimicrobial metal ion source may be in the form of microparticles and, preferably, nanoparticles, especially relative large surface area micro- and nano-particles, of the antimicrobial metal, it is preferred that the antimicrobial metal ion source be one that readily releases the antimicrobial metal ion in the presence of water. Thus, preferred antimicrobial metal ion sources are inorganic and organic compounds that are soluble in and/or dissociate, i.e., release the antimicrobial metal ion, in water. Another preferred antimicrobial metal ion source are those antimicrobial agents that release the antimicrobial metal ion through an ion-exchange.

Antimicrobial metal ion sources that are soluble in and/or readily dissociate in water are typically in the form of simple salts or organometallic compounds of the antimicrobial metals such as the oxide, sulfide, chloride, bromide, carbonate, nitrate, phosphate, dihydrogen phosphate, sulfate, oxalate, acetate, citrate, benzoate, thiosulfate and the like. Specific examples include silver nitrate, silver acetate, cupric oxide, cuprous oxide, zinc acetate and zinc oxide. More recent attention has focused on the organometallic compounds derived from silver and various carboxylic acids, especially citric acid, acetic acid and the like, including silver citrate, silver dihydrogen citrate, tri-silver citrate and the like. Especially preferred are the silver citrates prepared though electrolysis as shown in Arata et. al., (U.S. Pat. No. 6,197,814, U.S. Pat. No. 6,583,176, and US 2005/0245605). Although simple salts and organometallic compounds are useful, they tend to be short lived due to quick and/or essentially uncontrolled dissolution.

Alternatively, the antimicrobial agent may be in the form of a water soluble glass containing the antimicrobial agent or compound. These glasses, especially the silver glasses, are well known and are described in, e.g., Ishii et. al.—U.S. Pat. No. 6,831,028; Namaguchi et. al. U.S. Pat. No. 6,939,820; Nomura—U.S. Pat. No. 6,593,260; Shimiono et. al.—U.S. Pat. No. 5,290,544; Gilchrist—U.S. Pat. No. 5,470,585; and Drake—U.S. Pat. No. 4,407,786, which are incorporated herein by reference. They are characterized as being similar to typical glasses except that the traditional glass former, silicon dioxide, is replaced, in whole or in part, with phosphorus pentoxide ($P_2O_5$) as the principal glass former and they further comprise an antimicrobial metal or metal ion source. Other components include various oxides including, for example, CaO, $Na_2O$, MgO, $Al_2O_3$, ZnO, $B_2O_3$, etc. Typically these compositions will have from about 35 to about 75 mole percent, preferably from about 40 to about 60 mole percent, of the phosphorous pentoxide and from about 5 to about 55 mole percent, preferably from about 10 to about 40 mole percent, of a metal oxide, e.g., a Group IA or Group IIA metal oxide such as sodium oxide or calcium oxide. Antimicrobial properties are achieved by incorporation of water-soluble, simple metal salts of silver and/or copper, such as silver oxide and cupric oxide. The antimicrobial additive is present in the glass in the range of from about 1 to about 20% by weight, preferably from about 3 to about 15% by weight, based on the total weight of the antimicrobial water soluble glass.

Antimicrobial water soluble glasses are available from a number of sources including Ishazuka Glass Co., Ltd., the latter selling silver glass under the tradename "Ionpure." Antimicrobial glasses dissolve and/or swell upon exposure to water, including, though more slowly, atmospheric moisture, thereby releasing or making available the antimicrobial metal ion source within the glass. By suitable adjustment of the glass composition, the dissolution rates in water can be controlled, thereby controlling the release of the antimicrobial metal ions and, hence, extending their longevity.

The antimicrobial agent may also be in the form of an ion-exchange type antimicrobial agent or combinations of such agents. Ion-exchange type antimicrobial agents are typically characterized as comprising a ceramic particle having ion-exchanged antimicrobial metal ions, i.e., the antimicrobial metal ions have been exchanged for (replaced) other non-antimicrobially effective ions in and/or on the ceramic particles. Additionally these materials may have some surface adsorbed or deposited metal; however, the predominant antimicrobial effect is as a result of the ion-exchanged antimicrobial metal ions.

Antimicrobial ceramic particles include, but are not limited to zeolites, calcium phosphates, hydroxyapatite, zirconium phosphates and other ion-exchange ceramics. These ceramic materials come in many forms and types, including natural and synthetic forms. For example, the broad term "zeolite" refers to aluminosilicates having a three dimensional skeletal structure that is represented by the formula: $XM_2/nO$—$Al_2O_3$—$YSiO_2$—$ZH_2O$ wherein M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange antimicrobial agents may incorporate most any antimicrobial metal ions, including those mentioned above. Most commonly, though silver ions or silver ions in combination with zinc and/or copper ions are used. The amount of antimicrobial metal ion is generally in the range of from about 0.1 to about 25 wt %, preferably from about 0.3 to about 20 wt %, most preferably from about 2 to about 10 wt %, based upon 100% total weight of ceramic carrier. Where other antimicrobial metal ions are present, the makeup will be from about 0.1 to about 15 wt % of silver ions and from about 0.1 to about 15 wt % of copper and/or zinc ions. These ion-exchange type antimicrobial agents may also have incorporated therein ion-exchanged ammonium ion for improved color stability. If present, the ammonium ion may be present at a level of up to about 20 wt % of the carrier; however, it is desirable to limit the content of ammonium ions to from about 0.5 to about 2.5 wt %

All of the foregoing ion-exchange type antimicrobial agents are widely available and well known to those skilled in the art. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717 and 5,405,644. Antimicrobial zeolites containing antimicrobial metal ions are described in, e.g., U.S. Pat. Nos. 4,911,898; 4,911,899 and 4,938,958. Especially preferred ion-exchange antimicrobial agents are the antimicrobial zeolites available from AgION Technologies, Inc., of Wakefield, Mass., USA including, but not limited to product numbers AW10D (0.6% by weight of silver ion-exchanged in Type A zeolite particles having a mean average diameter of about 3μ, AG10N and LG10N (2.5% by weight of silver ion-exchanged in Type A zeolite particles having a mean average diameter of about 3μ and 10μ, respectively); AJ10D (2.5% silver, 14% by weight zinc, and between 0.5% and 2.5% by weight ammonium ion-exchanged therein in Type A zeolite having a mean average diameter of about 3μ); AK10D (5.0% by weight of silver ion-exchanged in Type A zeolite particles having a mean average diameter of about 3μ) and AC10D (6.0% by weight of copper and 3.5% by weight silver ion-exchanged in Type A zeolite particles having a mean average diameter of about 3μ).

As noted above, a single antimicrobial agent may be employed or a combination of such agents may be employed. For example, it may be desirable to employ a combination of an antimicrobial salt or organometallic compound with a water soluble glass and/or an ion-exchange type antimicrobial agent. Here the former provides for quick release and antimicrobial efficacy, especially if the salt or compound is readily soluble, whereas the latter provides a slower release and, thus, longer term efficacy.

Generally speaking, the amount of the antimicrobial agent to be combined with the wettable cake forming inorganic material will be from about 1 to about 50 parts, preferably from about 2 to about 20 parts, most preferably from about 5 to about 10 parts by weight of the antimicrobial agent (or combination of antimicrobial agents) per 100 parts by weight of the wettable cake forming inorganic material.

Normally, and preferably, the novel antimicrobial additives of the present invention will consist essentially of the antimicrobial agent and the wettable cake forming inorganic material; however, other additives typical of such cake forming materials in their normal end-use applications, such as colorants, plasticizers, and the like, may also be present. The inclusion of a color or coloring agent may be especially important in those applications where the additive is added to a colored cement, mortar, cementitious composition or hybrid cementitious composition and there is concern that the uncolored individual antimicrobial additive particles may affect the appearance of the final product. Here the antimicrobial additive particles may be matched to the color of the matrix material into which they are to be incorporated.

Additionally, the formed antimicrobial additive particles may further comprise water. In this respect the wettable cake-forming component of the particles may be in their hydrated or hemi-hydrated form. Since residual moisture is typically present in those cakes that are formed from a slurry in water, such particles may be dried prior to use to remove any residual water. On the other hand, it may be desirable to allow the residual water to remain; otherwise, wetting of the particles may take longer and, therefore, it may take longer for the antimicrobial properties to manifest themselves. It is also contemplated that one may add various wetting agents or surfactants, especially to the water used in forming the cake materials, in order to improve and/or accelerate wetting. Such wetting agents and surfactants are well known and widely available and would be used in conventional amounts.

The antimicrobial additive particles of the present invention may be made in a number of ways, as will be readily apparent to those skilled in the art. For example, the antimicrobial agent may be added to the dry blend of the cake-forming inorganic material before the addition of water. Alternatively, the antimicrobial agent may be added to a slurry of the cake-forming material in water. The former is preferred as many of the antimicrobial agents, especially those in fine powder form such as the ion-exchange type agents, have a tendency to clump-up or agglomerate upon addition to the slurry or to water, requiring excessive mixing in order to break up clumps of antimicrobial agents. Failure to evenly distribute the antimicrobial agent may lead to hot spots that, over time, cause increased discoloration, as well as an overall decrease in the concentration the antimicrobial agent in the novel additive particles free of such agglomerated materials. Dry blending simply ensures a more evenly distributed antimicrobial agent in the mix before the addition of water.

Once the slurry, preferably a homogeneous slurry, of the antimicrobial agent and the cake-forming material is formed, it is allowed to harden. For most cake-forming compositions, especially those based on the calcium minerals such as gypsum, calcium hydroxide, Portland cement and the like, hardening occurs by a chemical reaction, "setting", involving the water. Here the slurry may be allowed to stand in the mixer vessel or is preferably poured onto a flat surface or in a mold to form a slab or slab-like layer of the material. The latter is especially beneficial with kalsomine materials to allow cure or setting by carbonatation. The higher surface area helps speed up the reaction and, in the case of excess water, evaporation and, consequently, cure or hardening of the composition. Alternatively, the slurry may be placed in molds or whatever and pressed and/or baked to hasten the cure or hardening of the same. In the case of the clays, especially clay, china clay and kaolin clay, it is desirable to allow the slurry to harden to a green state and then fire the green state material in a high temperature kiln or oven. While the green state materials have certain structural integrity, that integrity can be lost rather quickly when the antimicrobial clay-based additives are incorporated into water or a water containing mixture. The fired clay materials maintain good porosity while being irreversible to the water, i.e., maintaining their particle structure.

Once the solid cake is formed, it is then broken up and crushed and/or ground to form the antimicrobial additive particles. The resultant antimicrobial additive particles generally have average diameters of at least 10, preferably at least 20, times that of the antimicrobial agent. Preferably, the crushing is of a controlled nature to produce particle sizes appropriate for and consistent with the intended use. Most preferably, the crushed material is subjected to screening to remove excessively large particles and/or to isolate the desired particle size or range of particle sizes for the intended application. For example, a cement for use in structural applications such as walls, building pads or slabs, walkways, etc., may use large particles sizes, perhaps on the order of the size of beach sand or larger, for example, on the order of 500-2000 microns and larger: perhaps as large as an inch or so. Other applications, such as floor coatings and the like, will want a smaller grain, on the order of a few hundred microns or less, to avoid surface imperfections or texturing.

As noted above, the particle size of the antimicrobial additive of the present invention may vary widely depending upon the end-use application. Generally speaking, the particle size of the novel antimicrobial additives of the present invention will be in the range of from 20 to 5000 microns, preferably from 50 to 2000 microns, most preferably from 100 to 500 microns. Such particle size ranges are especially suited for the novel antimicrobial additive particles to be incorporated into hybrid cementitious compositions as described below.

The novel antimicrobial additives of the present invention may be employed in any cement, mortar, cementitious, hybrid cementitious or like compositions. Although technically cementitious compositions, as used herein and in the appended claims, the terms "cement(s)" and "mortar(s)" refer to the base materials with typical additives such as colorants, plasticizers, anti-foaming/defoaming agents and the like. "Cementitious compositions", on the other hand, is used to refer to cements and mortars (with our without the traditional additives) in combination with one or more aggregate materials and/or fillers. As noted above, the term "hybrid cementitious compositions" refers to any of the foregoing, i.e., cements, mortars, and filler and/or aggregate containing cements and mortars further containing, in the cured state, a polymer resin, for example, an epoxy resin or polyurethane resin, that is either cured or polymerized in-situ or added in the form of an emulsion or suspension, as discussed in greater detail below.

When employed in cements, mortars, cementitious compositions and hybrid cementitious compositions, the novel antimicrobial additive particles of the present invention serve as reservoirs of the antimicrobial metal ions since substantially all of the antimicrobial source in the wettable, caked particle is available. In another respect, especially in those cements, mortars, cementitious compositions and hybrid cementitious compositions having a low degree of porosity and/or having a high level of polymer in the cured composition (in the case of those hybrid cementitious compositions having a curable or polymerizable organic component), they, surprisingly, enhance the antimicrobial efficacy, as evidenced by ion release, as compared to similar compositions employing the same amount of the same antimicrobial agent but in its neat form, i.e., not in the cake matrix.

Suitable cements, mortars and cementitious compositions, as well as aforementioned hybrid cementitious compositions, are all well known and widely available. Exemplary cements and mortars include a) Portland cement, b) rapid hardening cements characterized by a high alumina content, c) low-heat cements characterized by high dicalcium silicate and tetracalcium alumino ferrite content and low tricalcium silicate and tricalcium aluminate content, d) sulphate resisting cements characterized by unusually high tricalcium silicate and dicalcium silicate and unusually low tricalcium aluminate and tetracalcium alumino ferrite content, e) Portland blast-furnace cement characterized by a mixture of Portland cement clinker and granulated slag; f) masonry cements characterized by mixtures of Portland cement and one or more of the following: hydrated lime, granulated slag, pulverized limestone, colloidal clay, diatomaceous earth or other finely divided forms of silica, calcium stearate and paraffin; g) natural cements, h) lime cements characterized by the oxide of calcium in its pure or unpure form, with our without argillaceous material; i) selenitic cement characterized by the addition of 5-10% plaster of Paris to lime, j) pozzolanic cement characterized by the mixture of pozzolana, trass kieselguhr, pumice, tufa, and santorin earth or granulated slag with lime mortar; and k) calcium sulfate cements characterized by those depending on the hydration of calcium sulphate including plaster of Paris, Keene's cement and Parian cement.

Cementitious compositions vary widely in compositional make-up and, consequently, performance and physical properties. Two markedly different applications for cementitious compositions include the formation of synthetic stone, especially for countertops and the like, and durable flooring and floor coatings. As noted, cementitious compositions typically comprise a mortar or cement and an aggregate or aggregate mix or one or more fillers or both. Suitable aggregate materials include crushed and natural stones and minerals or mixtures thereof, including stones and minerals of different sizes. Exemplary aggregates, especially for the production of synthetic stone, include quartz, granite, feldspar, marble, quartzite, and a mixture thereof. Other suitable aggregates, especially for structural applications and the like, include traditional stone and crushed stone, pebbles, river rocks and the like. Suitable fillers include sand, clay, fumed silica, silicate flakes, fly ash, calcium carbonate, broken ceramics, mica, broken glass, glass beads, glass spheres, mirror fragments, steel grit, aluminum grit, carbides, plastic beads, pelletized rubber, ground polymer composites (e.g., acrylics encasing copper filings), wood chips, sawdust, mixtures of any two or more of the foregoing and the like.

The amount and selection of the aggregate and/or filler will depend upon the intended end-use application for the cementitious composition itself. Generally, the amount will be from about 5 to about 10,000 parts by weight, preferably from about 10 to about 5000 parts by weight based on 100 parts by weight of the base concrete or mortar into which they are to be incorporated. In use, the aggregate and/or filler may be pre-blended or pre-mixed with the cement or mortar base prior to addition of the water or they may be added to the slurry of the cement or mortar during use. Alternatively, one or all aggregates and/or fillers or portions thereof may be dry-blended with the cement or mortar and the remainder added to the slurry of the cement or mortar at the time of use. Most commonly, especially where the aggregate or filler is of substantial particle size, e.g., 3 mm or more in diameter, the aggregate and/or filler material is dry-blended and the mixture added to the slurry at the time of use.

Hybrid cementitious compositions suitable for use in the practice of the present invention also include those hybrid cement, mortar and aggregate and/or filler containing cementitious systems that further incorporate a resin or polymer emulsion or a polymerizable/curable organic resin composition at the time of use. Typically, these hybrid cementitious compositions are multi-part systems whose multiple parts, particularly that part/those parts comprising or containing the organic resin, either in its polymerized state or, preferably, in its pre-polymer state, i.e., as reactive monomers, dimmers, trimers, oligomers and/or pre-polymers, etc., typically, in solution, suspension or as an emulsion, are mixed at the time of use. In the case of solutions, suspensions or emulsions, the solvent or emulsion/suspension medium is preferably water; however, it may also be a reactive diluent that polymerizes concurrent with or co-polymerizes with the prepolymer resin. And, although the hybrid cementitious compositions may be based on a thermoplastic resin, it is preferred that the resin be a thermosetting, i.e., cross-linking, resin. Exemplary resins include the unsaturated polyester resins, vinyl acetate resins, epoxy resins and polyurethanes. Such hybrid cementitious compositions typically have from about 20 to 60%, preferably from about 30 to 50%, resin based on the total weight of the composition.

In use, polymerization/cure and/or cross-linking of the polymer resin is effected by environmental factors, e.g., heat generated by the cure or setting of the cement itself or water present in the cement slurry, or by the addition of co-reactive species, hardeners, and the like, as appropriate. The latter is typical of two-part curable resins wherein the two parts are maintained isolated from one another until the time of use. Exemplary and preferred two-part resins are the epoxy resins and polyurethanes. Especially preferred hybrid cementitious compositions are those based on polyurethane resins, particularly those derived from an isocyanate and/or an isocyanate functional prepolymer and an isocyanate reactive organic compound, most especially a diol, a polyol or a combination of both. Such compositions are well known and are described in, e.g., Shearing et. al.—U.S. Pat. No. 3,763,070 and U.S. Pat. No. 4,211,680 and Alexander et. al.—U.S. Pat. No. 4,127,548, all of which are incorporated herein, in their entirety, by reference. Furthermore, these hybrid cementitious compositions are commercially available from such sources as BASF Corporation of Florham Park, N.J.; Bayer Polymers LLC Americas of Pittsburgh, Pa., Sherwin Williams Company of Cleveland, Ohio; and Garon Products, Inc. of Wall, N.J.

Although the novel antimicrobial additives of the present invention may be added to the resin component or concurrent with the addition of the resin component and, if applicable, water, to the dry components of the hybrid cementitious compositions, it is preferred that it be dry blended with one or more of the non-resinous components of the hybrid systems prior to use. Addition of the antimicrobial additive to the resinous component may lead to uneven and inconsistent antimicrobial performance due to clumping or a settling of the same in the liquid components, especially where the resinous component(s) are of low or relatively low viscosity.

Generally speaking, at the time of preparing the improved antimicrobial cements, mortars, cementitious compositions and hybrid cementitious compositions of the present invention for use, these compositions will typically comprise, 100 parts by weight of the cement or mortar base, 10 to 75 parts by weight water, 1 to 50 parts by weight of the antimicrobial additive of the present invention and, if present, 10 to 10,000 parts by weight of the aggregate/filler, and 5 to 5,000 parts by weight of the resin (based on the weight of the solids or polymerizable/curable components). Of course, the specific formulation will depend upon the end-use application and performance profiles needed. In addition, these compositions may further contain various other additives and ingredients commonly found in such cements, mortars, cementitious compositions and hybrid cementitious compositions provided that they do not interact with the antimicrobial metal ions or, if such interaction occurs, their presence is low and is insufficient to impede the antimicrobial efficacy of the antimicrobial additives herein. Exemplary of such additives are colorants, pigments, plasticizers, foam suppressors and defoaming agents, and the like. The latter are present in such amounts as is typical in the industry.

Alternatively or in addition to the foregoing, the antimicrobial cements, mortars, cementitious and hybrid cementitious compositions may further contain a neat antimicrobial agent, in addition to the novel antimicrobial agents of the present invention, for supplemental antimicrobial activity and/or to increase the initial level of activity. Any of the neat antimicrobial agents employed in making the novel antimicrobial agents of the present invention may be added and it may be the same or a different antimicrobial agent from what is employed in the novel additive.

Furthermore, those compositions of the present invention which employ an ion-exchange type antimicrobial agent, either in the novel antimicrobial additives of the present invention or as a supplemental antimicrobial agent as mentioned above, may also contain a dopant as a ready source of cations to complete the ion exchange. In this respect, such dopants facilitate the release and transport of the antimicrobial metal ion from the ion-exchange carrier particle. Preferred dopants include, but are not limited to, inorganic salts of sodium such as sodium nitrate. For example, if sodium nitrate is used with a silver containing ion-exchange type antimicrobial agent, the sodium nitrate dissociates providing sodium ions which exchange with the antimicrobial silver ions, thereby releasing the silver ion for transport to the surface.

The antimicrobial cements, mortars, cementitious compositions and hybrid cementitious compositions of the present invention have a wide array of uses. In essence, they can be used in most any application and for most any purpose that such compositions without the antimicrobial additive are used. However, because of the added cost factor of the antimicrobial additive, use for many applications may not be commercially feasible; though certainly technically feasible. For example, while it may be desirable to produce antimicrobial concrete for foundations, especially in areas where damp and moldy basements are a problem; currently, the added benefit is vastly outweighed by the incremental cost increase in the concrete. Thus, their commercial use, at least at the present time is focused on those applications where the cement, mortar or cementitious product is employed in a relatively thin layer, perhaps as an overcoat, and/or in high value added applications. In particular, these compositions are especially desirable for use in the production of cement countertops, in the production of artificial stone slabs and stock materials, in floor coatings, and the like.

As noted and as evidenced by the following examples, the use of the novel antimicrobial additives in cements, mortars, cementitious compositions and hybrid cementitious compositions provides for an efficient use of the antimicrobial agent, providing, in many instances, surprisingly high antimicrobial performance as compared to the simple addition the same quantity (based on antimicrobial metal ion content) of the neat antimicrobial agent to the same cement, mortar, cementitious composition or hybrid cementitious composition. It has also been found that one is able to further improve the performance from a cost benefit perspective by making adjustments in the particle size, concentration of the antimicrobial agent in the additive particles and the amount of the additive particles to be employed. This is especially important in commodity, high cost intolerant applications and can be accomplished by reducing the particle size of the antimicrobial additive particles so as to provide a higher density of such particles at the same weight loading. Similarly, by keeping the concentration of the antimicrobial agent in the additive particles on the lower end of the scale, one can use a higher loading of particles to once again increase the density of the particles. A higher density means more particles across any given surface area which, especially in the case of non-porous and/or non-wetting or poorly wetting solidified or cured cements, mortars, cementitious compositions and hybrid cementitious compositions, means more sites of available antimicrobial metal ions. Thus, through simple trial and error in light of the teachings set forth herein, one may make adjustments to the concentration of the antimicrobial agent in the cake-forming material, to the particle size of the antimicrobial additive and to the loading of the antimicrobial additive particles in the cement, mortar, cementitious composition or hybrid cementitious composition in order to attain the best cost/benefit needed to make a commercially viable product. Generally speaking, the antimicrobial cements, mortars, cementitious compositions and hybrid cementitious compositions of the present invention must be capable of providing efficacious antimicrobial performance. Typically, a composition that is capable of eluting at least 20 ppb of the antimicrobial metal ion or ions in accordance with the test method described below are found to be efficacious.

The following examples are merely illustrative of the invention and are not to be deemed limiting thereof. Those skilled in the art will recognize many variations that are within the spirit of the invention and scope of the claims.

In the following examples, ion elution was evaluated as follows: The compositions were allowed to cure for at least 24 hours after which 1" by 1" test pieces of the cured materials were cut using a diamond saw. The test pieces were coated on the back and sides with molten paraffin wax leaving just the 1" by 1" surface exposed. Each test piece was then immersed in 40 ml of an 0.8% sodium nitrate solution for 24 hours. The silver concentration of each solution was then determined by atomic absorption spectroscopy on a Perkin Elmer atomic absorption spectrophotometer and the results reported in ppb silver.

Example 1-3 and Comparative Examples CE1-CE2

An antimicrobial gypsum was prepared by adding 10 grams of a silver zeolite, AgION AK10D antimicrobial, from AgION Technologies, Inc. of Wakefield, Mass., to 100 grams of calcium sulfate hemihydrate, Playbox Plaster of Paris, available from Specialized Building Products of Orange, Calif. The mixture was dry blended to give a substantially homogenous mixture and then added to 50 ml of water and thoroughly mixed. The resulting smooth uniform slurry was allowed to set and the set material crushed and ground to a fine mixture in a mortar and pestle. The fine mixture was then screened using an 80 mesh screen to remove any remaining large particles. 15 grams of the resulting material was placed in a seal grip bag and labeled wet gypsum (WG). The remaining screened materials were placed in an oven at 50° C. and dried for 3 hours. 12 grams of this material was then placed in a seal grip bag and labeled dry gypsum (DG). Finally, the remainder of the screened material was then placed in an oven at 125° C. and allowed to dry overnight. The material was then placed in a seal grip bag and labeled anhydrous gypsum (AG).

Each of the foregoing antimicrobial gypsum additive materials was incorporated into a conventional polyurethane concrete slurry in an amount so as to provide a 1% by weight concentration of the antimicrobial agent in each formulation (0.05% silver). The cementitious polyurethane comprised an aqueous polyol emulsion, an isocyanate, and a dry mix of a conventional cement material containing Portland cement vertical hydrated lime and aggregate. Comparative compositions, one comprising the neat polyurethane concrete slurry (i.e., no antimicrobial additive) and another comprising the neat polyurethane concrete slurry and 1% by weight of the neat antimicrobial agent (AK10D) were also prepared. In preparing these materials, the antimicrobial additive was added to the dry mix of the cement material and uniformly blended before being added to the combined mix of the polyol and isocyanate. Each composition was thoroughly mixed and then allowed to cure for at least 24 hours. Following cure, 1" by 1" test samples were cut from the cured mass and evaluated for silver elution in accordance with the method described above. One set of test pieces (one test piece of each composition) was lightly sanded/abraded by hand using 600 grit sandpaper and a second set remained unsanded. Each test piece was then evaluated for ion elution. The results of the silver elution study are as reported in Table 1.

Surprisingly, despite the presence of the same amount of antimicrobial agent (1% by weight AgION AK10d, 0.05% silver) in each composition, those compositions made with the novel antimicrobial additives of the present invention provided a markedly higher ion elution than those samples incorporating the neat antimicrobial agent. As also seen, light sanding further increased the ion elution.

TABLE 1

| Example | Antimicrobial Additive | Silver Release (ppb) | |
| --- | --- | --- | --- |
| | | Unsanded | Sanded |
| CE1 | None | 0 | 0 |
| CE2 | AK10D | 6.2 | 75 |
| E1 | WG | 31 | 300 |
| E2 | DG | 380 | 190 |
| E3 | AG | 54 | 140 |

This latter finding is consistent with the likelihood of the polyurethane resin of the cement mixture forming a film over the particles of the antimicrobial agent and/or on the surface of the cured cement material. Sanding mimics normal wear and erosion of such compositions when employed as floor coatings or coatings of work surfaces and the like that are subjected to wear and/or repeated washings and scrubbing. Even without sanding, the polyurethane cement incorporating the novel antimicrobial additives of the present invention provided sufficient ion release as to be deemed efficacious whereas the samples prepared with the neat antimicrobial agent did not.

Examples 5-8, Comparative Examples CE3-CE5

Two sets of antimicrobial gypsum additive particles were made as in Example 1 except that the amount of the antimicrobial agent was increased to give a concentration of 7.7 wt % and 20.0 wt % AgION AK10D in gypsum. Again the ground particles were dried at 40° C. overnight and then sieved using an 80 mesh screen to remove large particles.

A second set of comparative and inventive antimicrobial polyurethane cements were prepared and evaluated for ion release. This time the polyurethane cement matrix evaluated was that sold by Sherwin Williams Company of Cleveland, Ohio under the tradename Fastop S. This too is a three part system comprising an aqueous emulsion of a polyol (Part A), an isocyanate (Part B) and a cement mix (Part C). The antimicrobial agents evaluated were pre-blended with the Part C to obtain a substantially homogeneous mixture. Parts A and B were then mixed in their proper proportions for about 1 minute and then the Part C/antimicrobial mixture added with thorough mixing. The mixtures were then placed into a plastic tray and allowed to cure for at least 3 days. Samples were then cut and ion elution studies performed. The formulations of each sample and the results of the ion release studies were as presented in Table 2.

TABLE 2

| | Example | | | | | | |
| --- | --- | --- | --- | --- | --- | --- | --- |
| Ingredient | CE3 | CE4 | CE5 | 5 | 6 | 7 | 8 |
| Part A | 56.9 | 56.9 | 56.9 | 56.9 | 56.9 | 56.9 | 56.9 |
| Part B | 50 | 50 | 50 | 50 | 50 | 50 | 50 |
| Part C | 302 | 302 | 302 | 302 | 280 | 302 | 280 |
| Gypsum w/ AK10D @ 7.7 wt % | — | — | — | 22.1 | 44.2 | — | — |
| Gypsum w/ AK10D @ 20 wt % | — | — | — | — | — | 8.4 | 17 |
| AK10D | 1.7 | 3.4 | 6.8 | — | — | — | — |
| (% AK10D) | 0.4 | 0.8 | 1.6 | 0.4 | 0.8 | 0.4 | 0.8 |
| Silver ppb | 2.1 | 2.2 | 61 | 47 | 184 | 2.7 | 3.6 |

As seen in Table 2, once again the inventive antimicrobial additives of the present invention provided markedly improved antimicrobial metal ion release as compared to the same formulations employing the neat antimicrobial agent. Surprisingly, the inventive compositions employing the higher loaded antimicrobial gypsum particles performed only as well as the neat antimicrobial agent. It is believe that this resulted from the much lower density of particles in the polyurethane cement. Indeed, these compositions have less than 40% the number of particles in Examples 5 and 6. As those skilled in the art will readily appreciate, fewer particles in the overall composition means fewer particles at the surface of the test pieces from which the antimicrobial metal ions are released. Though many particles are within the body of the test pieces, the results of the sanded versus unsanded samples in Example 1 suggest that these are not available or readily available for contributing to the ion release of the sample. In essence, it is believed that the polyurethane of the cement composition is inhibiting ion release and/or transport from within the sample.

On the other hand, these compositions would be expected to have a much longer life since the individual particles at the surface hold a much higher concentration of the antimicrobial metal ions as compared to the particles of Examples 5 and 6 and multifold more than in the neat antimicrobial agent particles. In the latter, each neat zeolite particle holds 5% silver whereas the antimicrobial gypsum particles hold multiple zeolite particles, each of which holds 5% silver.

In any event, it will be appreciated that one should be able to increase the ion release of those compositions employing the 20% loaded gypsum antimicrobial additive simply by reducing the particle size. More particles will increase their density and, thus, increase the number at the surface of the test piece.

Although the present invention has been described with respect to the foregoing specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles.

We claim:

1. An antimicrobial additive in the form of discrete particles of a wettable, caked inorganic material of from 20 to 5000 microns, said discrete particles consisting essentially of:

a) gypsum, gypsum cement, calcium hydroxide, calcium carbonate, chalk clay, Portland cement, kalsomine, or calcite as the matrix phase material having incorporated or dispersed therein
b) from about 1 to about 50 parts by weight, based on 100 parts by weight of (a), of at least one antimicrobial metal ion-containing inorganic or organometallic antimicrobial agent capable of releasing antimicrobial metal ions in the presence of water in an antimicrobially effective amount; and
c) optionally, colorants, plasticizers, pigments, foaming suppressors, defoaming agents, antifoaming agents, surfactants, wetting agents, residual water, and combinations thereof;
wherein the antimicrobial metal ion is at least one of silver, copper, zinc, tin, gold, mercury, lead, iron, cobalt, nickel, manganese, arsenic, antimony, bismuth, barium, cadmium, chromium and thallium and the antimicrobial agent is in the form of a salt, an organometallic compound, a water soluble glass containing a source of the antimicrobial metal ion(s), an ion-exchange antimicrobial agent comprising a ceramic carrier particle with ion-exchangeable antimicrobial metal ions, or combinations thereof; provided that when the antimicrobial agent is in the form of discrete particles dispersed in (a), the particle size of the antimicrobial agent is no more than one-tenth that of the particle size of the antimicrobial additive;
wherein said antimicrobial additive particles are capable of maintaining, for the most part, their particle form while being incorporated into cements, mortars and cementitious or hybrid cementitious compositions.

2. The antimicrobial additive of claim 1 wherein the matrix phase material is gypsum or a gypsum containing material.

3. The antimicrobial additive of claim 2 wherein the gypsum or gypsum containing material is hydrated, hemi-hydrated or dried.

4. The antimicrobial additive of claim 1 wherein the antimicrobial agent is present in the form of discrete particles which are micro-sized or nano-sized or both and have an average particle size of no larger than one twentieth that of the antimicrobial additive.

5. The antimicrobial additive of claim 1 wherein the antimicrobial agent is a salt or an organometallic compound of an antimicrobial metal.

6. The antimicrobial additive of claim 5 wherein the salt or organometallic compound is selected from the oxides, sulfides, chlorides, bromides, carbonates, nitrates, sulfates, phosphates, dihydrogen phosphates, oxalates, acetates, citrates, benzoates, and thiosulfates of the antimicrobial metals.

7. The antimicrobial additives of claim 5 wherein the antimicrobial agent is selected from silver nitrate, silver acetate, cupric oxide, cuprous oxide, zinc acetate, zinc oxide, silver citrate, silver dihydrogen citrate, and tri-silver citrate.

8. The antimicrobial additive of claim 1 wherein the antimicrobial agent is a water soluble glass containing an antimicrobial metal or metal ion.

9. The antimicrobial additive of claim 1 wherein the antimicrobial agent is an ion-exchange antimicrobial agent comprising ceramic particles having ion-exchanged antimicrobial metal ions.

10. The antimicrobial additive of claim 9 wherein the ceramic particles are selected from the group consisting of zeolites, hydroxyapatites, calcium phosphates, and zirconium phosphates.

11. The antimicrobial additive of claim 1 wherein the additive particles have a particle size of from 100 to 500 microns.

12. The antimicrobial additive of claim 1 wherein the antimicrobial metal ion is selected from the group consisting of silver, copper, zinc, and combinations of silver with zinc or copper or both.

13. The antimicrobial additive of claim 1 wherein the additive particles have a particle size of from 50 to 2000 microns and the antimicrobial agent is present in an amount of from about 2 to about 20 parts by weight based on 100 parts by weight of the matrix phase material.

14. A method of making an antimicrobial additive in the form of discrete particles of a wettable, caked inorganic material of from 20 microns up to one inch which particles are capable of maintaining, for the most part, their particle form while being incorporated into cements, mortars, and cementitious and hybrid cementitious compositions, said method comprising the steps of:
   i) forming a slurry of an inorganic wettable cake forming composition consisting essentially of (a) gypsum, gypsum cement, calcium hydroxide, calcium carbonate, chalk, clay, Portland cement, kalsomine, or calcite as the matrix forming material; (b) from about 1 to about 50 parts by weight, based on 100 parts by weight of (a), of at least one antimicrobial metal ion-containing inorganic or organometallic antimicrobial agent capable of releasing antimicrobial metal ions in the presence of water in an antimicrobially effective amount; and (c) optionally, colorants, plasticizers, pigments, foaming suppressors, antifoaming agents, defoaming agents, surfactants, wetting agents, residual water, or combinations thereof;
      wherein the antimicrobial metal ion is at least one of silver, copper, zinc, tin, gold, mercury, lead, iron, cobalt, nickel, manganese, arsenic, antimony, bismuth, barium, cadmium, chromium and thallium and the antimicrobial agent is in the form of a salt, an organometallic compound, a water soluble glass containing a source of the antimicrobial metal ion(s), an ion-exchange antimicrobial agent comprising a ceramic carrier particle with ion-exchangeable antimicrobial metal ions, or combinations thereof: provided that when the antimicrobial agent is not soluble in the slurry, its particle size in no more than one tenth that of the particles to be formed by the method;
   ii) allowing the composition to cure or harden to form a cake;
   iii) breaking, crushing and/or grinding the cake to form discrete particles thereof; and
   iv) either removing those particles exceeding a maximum particle size or isolating those particles of a set particle size or range of particle sizes, or both.

15. The method of claim 14 wherein the matrix phase material is gypsum or a gypsum containing g material.

16. The method claim 14 wherein the cure or hardening of the cake is accomplished by setting, carbonatation, pressing, heating or a combination of any two or all three such actions.

17. The method of claim 16 wherein the cure or hardening is effected by heating.

18. The antimicrobial additive of claim 1 wherein the amount of the antimicrobial agent is from about 2 to about 20 parts by weight.

19. The antimicrobial additive of claim 1 wherein the amount of the antimicrobial agent is from about 5 to about 10 parts by weight.

20. The antimicrobial additive of claim 1 wherein the antimicrobial agent is present as micro-sized or nano-sized particles or both.

21. The antimicrobial additive of claim 1 comprising discrete particles of from 50 to 2000 microns and from about 2 to about 20 parts by weight of the antimicrobial agent based on 100 parts by weight of the matrix phase material, wherein the particles of the antimicrobial agent are no more than one twentieth of the size of the antimicrobial additive particles.

22. The antimicrobial additive of claim 21 wherein the antimicrobial agent is an ion-exchange type antimicrobial agent comprising ceramic particles having ion-exchanged thereon antimicrobial metal ions.

23. The antimicrobial additive of claim 22 wherein the ceramic particles are selected from the group consisting of zeolites, hydroxyapatites, calcium phosphates, and zirconium phosphates.

24. The antimicrobial additive of claim 21 wherein the antimicrobial agent is an antimicrobial zeolite having ion-exchanged antimicrobial silver, copper or zinc ions or combinations of any two or all three ions.

25. The method of claim 14 wherein the amount of the antimicrobial agent is from about 2 to about 20 parts by weight.

26. The method of claim 14 wherein the amount of the antimicrobial agent is from about 5 to about 10 parts by weight.

27. The method of claim 14 wherein the antimicrobial agent is present in the form of discrete particles which are micro-sized or nano-sized or both and have an average particle size of no larger than one twentieth that of the antimicrobial additive.

28. The method of claim 14 wherein the additive particles to be formed have a particle size of from 50 to 2000 microns and the antimicrobial agent is present in an amount of from about 2 to about 20 parts by weight based on 100 parts by weight of the matrix phase material, wherein the particles of the antimicrobial agent are no more than one twentieth of the size of the antimicrobial additive particles.

29. The method of claim 28 wherein the antimicrobial agent is an ion-exchange antimicrobial agent comprising ceramic particles having ion-exchanged thereon antimicrobial metal ions.

30. The method of claim 29 wherein the ceramic particles are selected from the group consisting of zeolites, hydroxyapatites, calcium phosphates, and zirconium phosphates.

31. The method of claim 28 wherein the antimicrobial agent is an ion-exchange antimicrobial agent comprising ceramic particles having ion-exchanged thereon antimicrobial metal ions.

32. The method of claim 14 wherein the antimicrobial agent is an antimicrobial zeolite having ion-exchanged antimicrobial silver, copper or zinc ions or combinations of any two or all three ions.

33. The antimicrobial additive of claim 1 wherein the antimicrobial agent is soluble in water and the additive particle is formed from a slurry of the matrix material (a) having dissolved therein the antimicrobial agent (b).

34. The antimicrobial additive of claim 1 wherein the clay is selected from the group consisting of kaolin clay or china clay.

35. The method of claim 14 wherein the antimicrobial agent is soluble in the slurry.

36. The method of claim 14 wherein the clay is selected from the group consisting of kaolin clay or china clay.

* * * * *